US009433573B2

(12) United States Patent
Martin et al.

(10) Patent No.: US 9,433,573 B2
(45) Date of Patent: *Sep. 6, 2016

(54) MICROFABRICATED NANOPORE DEVICE FOR SUSTAINED RELEASE OF THERAPEUTIC AGENT

(71) Applicant: Delpor, Inc., San Francisco, CA (US)

(72) Inventors: Francis J. Martin, San Francisco, CA (US); Anthony A. Boiarski, Hillard, OH (US)

(73) Assignee: Delpor, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/727,581

(22) Filed: Jun. 1, 2015

(65) Prior Publication Data

US 2015/0258017 A1 Sep. 17, 2015

Related U.S. Application Data

(60) Division of application No. 14/083,187, filed on Nov. 18, 2013, now Pat. No. 9,066,875, which is a continuation of application No. 13/098,067, filed on Apr. 29, 2011, now Pat. No. 8,603,076, which is a (Continued)

(51) Int. Cl.
*A61K 9/00* (2006.01)
*A61M 5/142* (2006.01)

(Continued)

(52) U.S. Cl.
CPC ........... *A61K 9/0004* (2013.01); *A61K 9/0024* (2013.01); *A61K 9/0097* (2013.01); *A61K 9/1694* (2013.01); *A61K 9/4808* (2013.01);

(Continued)

(58) Field of Classification Search
CPC ................. A61M 31/002; A61M 5/14276
See application file for complete search history.

(56) References Cited

U.S. PATENT DOCUMENTS 3,923,426 A 12/1975 Theeuwes
4,814,183 A 3/1989 Zentner (Continued)

FOREIGN PATENT DOCUMENTS

CN 1262096 A 8/2000
EP 0485370 A 5/1992

(Continued)

OTHER PUBLICATIONS

Burnett, "Immunoglobulins in the lung", Thorax, vol. 41, pp. 337-344 (1986).

(Continued)

*Primary Examiner* — Carlos Azpuru
(74) *Attorney, Agent, or Firm* — Judy M. Mohr; McDermott Will & Emery LLP

(57) ABSTRACT

A drug delivery device that includes a capsule for implantation into the body; the capsule further includes a reservoir for containing a substance such as a therapeutic agent, at least one port for allowing the substance to diffuse from or otherwise exit the reservoir, and a nanopore membrane in communication with the capsule at or near the exit port for controlling the rate of diffusion of the substance from the exit port. The device also includes an optional screen for providing structural stability to the nanopore membrane and for keeping the pores of the nanopore membrane clear. One embodiment of the drug delivery device includes an osmotic engine internal to the device for creating fluid flow through the device.

13 Claims, 6 Drawing Sheets

Related U.S. Application Data continuation of application No. 11/530,729, filed on Sep. 11, 2006, now Pat. No. 7,955,614, which is a continuation of application No. 10/243,787, filed on Sep. 13, 2002, now abandoned.

(60) Provisional application No. 60/371,290, filed on Apr. 9, 2002, provisional application No. 60/322,160, filed on Sep. 14, 2001.

(51) Int. Cl.

| | | |
|---|---|---|
| A61K 9/16 | (2006.01) | |
| A61M 5/168 | (2006.01) | |
| A61K 38/27 | (2006.01) | |
| A61M 31/00 | (2006.01) | |
| A61K 9/48 | (2006.01) | |
| A61K 38/02 | (2006.01) | |
| A61K 38/19 | (2006.01) | |

(52) U.S. Cl.
CPC .............. *A61K 38/02* (2013.01); *A61K 38/19* (2013.01); *A61K 38/27* (2013.01); *A61M 5/14276* (2013.01); *A61M 5/16804* (2013.01); *A61M 31/002* (2013.01)

(56) References Cited

U.S. PATENT DOCUMENTS

| | | | |
|---|---|---|---|
| 4,855,141 A | 8/1989 | Eckenhoff et al. | |
| 5,158,537 A | 10/1992 | Haak et al. | |
| 5,443,461 A | 8/1995 | Atkinson et al. | |
| 5,573,651 A | 11/1996 | Dasgupta et al. | |
| 5,628,993 A | 5/1997 | Yamagata et al. | |
| 5,651,900 A | 7/1997 | Keller et al. | |
| 5,770,076 A | 6/1998 | Chu et al. | |
| 5,798,042 A | 8/1998 | Chu et al. | |
| 5,874,099 A | 2/1999 | Dionne et al. | |
| 5,888,533 A | 3/1999 | Dunn | |
| 5,928,923 A | 7/1999 | Lal et al. | |
| 5,938,923 A | 8/1999 | Tu et al. | |
| 5,948,255 A | 9/1999 | Keller et al. | |
| 5,985,164 A | 11/1999 | Chu et al. | |
| 5,985,328 A | 11/1999 | Chu et al. | |
| 6,019,882 A | 2/2000 | Rakestraw et al. | |
| 6,044,981 A | 4/2000 | Chu et al. | |
| 6,113,938 A | 9/2000 | Chen et al. | |
| 6,221,654 B1 | 4/2001 | Quake et al. | |
| 6,270,672 B1 | 8/2001 | Turecek et al. | |
| 6,352,721 B1 | 3/2002 | Faour | |
| 6,416,642 B1 | 7/2002 | Alojoki et al. | |
| 6,482,306 B1 | 11/2002 | Yager et al. | |
| 6,955,670 B2 | 10/2005 | Martin et al. | |
| 7,259,020 B2 | 8/2007 | Sundberg et al. | |
| 7,799,197 B2 | 9/2010 | Hansford et al. | |
| 7,955,614 B2 | 6/2011 | Martin et al. | |
| 8,603,076 B2 | 12/2013 | Martin et al. | |
| 8,986,727 B2 | 3/2015 | Martin et al. | |
| 9,005,650 B2 | 4/2015 | Martin et al. | |
| 9,066,875 B2 | 6/2015 | Martin et al. | |
| 9,066,876 B2 | 6/2015 | Martin et al. | |
| 9,271,926 B2 * | 3/2016 | Martin ................. | A61K 9/0004 |
| 2003/0010638 A1 | 1/2003 | Hansford et al. | |
| 2003/0013186 A1 | 1/2003 | Martin et al. | |
| 2003/0064095 A1 | 4/2003 | Martin et al. | |
| 2004/0262159 A1 | 12/2004 | Martin et al. | |
| 2005/0118229 A1 | 6/2005 | Boiarski | |
| 2006/0191831 A1 | 8/2006 | Hansford et al. | |
| 2007/0077273 A1 | 4/2007 | Martin et al. | |
| 2011/0223233 A1 | 9/2011 | Martin et al. | |
| 2013/0211368 A1 | 8/2013 | Martin et al. | |
| 2014/0046287 A1 | 2/2014 | Martin et al. | |
| 2014/0079754 A1 | 3/2014 | Martin et al. | |
| 2014/0086972 A1 | 3/2014 | Martin et al. | |
| 2015/0174318 A1 | 6/2015 | Martin et al. | |
| 2015/0258017 A1 | 9/2015 | Martin et al. | |
| 2015/0258018 A1 | 9/2015 | Martin et al. | |

FOREIGN PATENT DOCUMENTS

| | | |
|---|---|---|
| GB | 2141737 A | 1/1985 |
| GB | 2178656 A | 2/1987 |
| JP | 62034576 A | 2/1987 |
| JP | 1299568 A | 12/1989 |
| JP | 2056417 A | 2/1990 |
| JP | H07500264 A | 1/1995 |
| JP | H09512250 A | 12/1997 |
| JP | H11506696 A | 6/1999 |
| WO | WO 93/06819 A1 | 4/1993 |
| WO | WO 95/22962 A1 | 8/1995 |
| WO | WO 95/24472 A1 | 9/1995 |
| WO | WO 96/40420 A1 | 12/1996 |
| WO | WO 97/25531 A | 7/1997 |
| WO | WO 00/09753 A1 | 2/2000 |
| WO | WO 01/10470 A1 | 2/2001 |
| WO | WO 01/30323 A2 | 5/2001 |
| WO | WO 01/51035 A1 | 7/2001 |
| WO | WO 02/103210 A1 | 12/2002 |
| WO | WO 2009/015329 A2 | 1/2009 |

OTHER PUBLICATIONS

Chu et al., "Silicon membrane nanofilters from sacrificial oxide removal", J. Microelectromechanical Sys., vol. 8, No. 1, p. 34-42 (1999).

Definition of "Control", in Websters New World College Dictionary, Third Edition, p. 303, (1996).

Definition of "Drug", in Hawley's Condensed Chemical Dictionary, Fourteenth Edition, p. 425, (2001).

Definition of "Hormone", in Hawley's Condensed Chemical Dictionary, Fourteenth Edition. p. 579, (2001).

Definition of "Insulin", in The Bantam Medical Dictionary, Revised Edition, Market House Books Ltd., p. 224 (1990).

Desai et al., "Microfabricated Immunoisolating Biocapsules", Biotechnol. Bioeng., vol. 57, pp. 118-120 (1998).

Desai et al., "Characterization of micromachined silicon membranes for immunoisolation and bioseparation applications", Journal of Membrane Science, vol. 159, pp. 221-231 (1999).

Grove, "BioMEMS and Nanotechnology: Opening up new opportunities for drug delivery" BioMEMS & Biomedical Nanotechnology World 2000, 1 page, (Sep. 25, 2000) *Abstract.*

Hassiepen et al., "The lifetime of insulin hexamers", vol. 77, No. 3, pp. 1638-1654 (1999).

Imai et al., "Direct preparation of anatase TiO2 nanotubes in porous alumina membranes", J. Mater. Chem., vol. 9, 2971-2972 (1999).

International Search Report from related PCT Patent Application No. PCT/US2002/018951 mailed on Oct. 21, 2002, Application now published as WO 2002/103210 on Dec. 27, 2002.

International Search Report from related PCT Patent Application No. PCT/US2002/029239 mailed on Jul. 17, 2003, Application now published as WO 2003/024357 on Mar. 27, 2003.

International Search Report from related PCT Patent Application No. PCT/US2004/034816 mailed on May 30, 2006, Application now published as WO 2005/039668 on May 6, 2005.

Kasianowicz et al., "Characterization of individual polynucleotide molecules using a membrane channel", PNAS, vol. 93, No. 24, pp. 13770-13773 (1996).

Kim et al., "Evaluation of electroosmosis and streaming potential for measurement of electric charges of polymeric membranes", J. Membrane Sci., vol. 116, pp. 149-159 (1996).

Kim et al., "Net Absorption Of IgG Via FcRn-Mediated Transcytosis Across Rat Alveolar Epithelial Cell Monolayers", Am. J. Physiol. Lung Cell. Mol. Physiol., vol. 287, pp. L616-L622 (2004).

Langer and Folkman, "Polymers for the sustained release of proteins and other macromolecules", Nature, vol. 263, No. 5580, pp. 797-800 (1976).

(56) References Cited

OTHER PUBLICATIONS

Langer and Peppas, "Present and future applications of biomaterials in controlled drug delivery systems", Biomaterials, vol. 2, pp. 201-214 (1981).
Martin et al., "Microfabricated drug delivery systems: Concepts to improve clinical benefit", Biomedical Microdevices vol. 3, No. 2, pp. 97-108 (2001).
Noormagi et al., "Zn(II) ions co-secreted with insulin suppress inherent amyloidogenic properties of monomeric insulin", Biochem. J., vol. 430, No. 3, 122, 511-518 (2010).
Product Information, "Insulin From Bovine Pancreas", from Sigma-Aldrich Catalog, Sigma Product No. I5500, I6634, I1882, and I4011, CAS No. 11070-73-8, 3 pages, (2003).
Response by Applicant in Inter Partes Reexamination, Applicant Arguments/Remarks Made in an Amendment, Reexamination Control No. 95/002,099, Patent Under Reexamination: 7,955,614, 25 pages, Mailed Dec. 21, 2012.
Response by Third Party Requestor, Comments After Non-final Action, Reexamination Control No. 95/002,099, Patent Under Reexamination: 7,955,614, 53 pages, Mailed Jan. 17, 2013.
Stemme et al., "New fluid filter structure in silicon fabricated using a self-aligning technique", Appl. Phys, Lett., vol. 53, No. 16, pp. 1566-1568 (1988).
Tan et al., "A nanoengineering approach for investigation and regulation of protein immobilization", ACS Nano., vol. 2, No. 11, pp. 2374-2378 (2008).
*The Bantam Medical Dictionary, Revised Addition*, Bantam Books, New York, ISBN 0-553-28498-3, pp. 224, (1990).
Turkenburg-Van Diepen, "Crystallographic studies of modified insulin: A thesis submitted to the University of York for the degree of doctor of philosophy", Department of Chemistry, University of York, Chapter 5, 154 pages, Sep. 1996, Downloaded from http://www.ysbl.york.ac.uk/~mgwt/thesis-tth/on Oct. 17, 2013.
U.S. Patent and Trademark Office, Form PTOL-2063 (Aug. 2006), Order Granting/Denying Requeat for Inter Partes Reexamination, Control No. 95/002,099, Patent Under Reexamination: 7,955,614, 24 pages, Mailed: Nov. 9, 2012.
U.S. Patent and Trademark Office, Form PTOL-2064 (Aug. 2006), Office Action in Inter Partes Reexamination, Control No. 95/002,099, Patent Under Reexamination: 7,955,614, 37 pages, Mailed: Nov. 9, 2012.
"What is the hydrodynamic radius ($R_H$)?", Malvern Instruments, Chapter: Dynamic Light Scattering, 3 Pages, Online article accessed on Dec. 4, 2014 from: http//:www.imbb.forth.gr/people/aeconomou/pdf/hydrodynamic_radius.pdf.

* cited by examiner

MICROFABRICATED NANOPORE DEVICE FOR SUSTAINED RELEASE OF THERAPEUTIC AGENT

CROSS-REFERENCE TO RELATED APPLICATIONS

This application is a divisional of U.S. application Ser. No. 14/083,187, filed Nov. 18, 2013, now allowed, which is a continuation of U.S. application Ser. No. 13/098,067, filed Apr. 29, 2011, now U.S. Pat. No. 8,603,076C1, which is a continuation of U.S. application Ser. No. 11/530,729, filed Sep. 11, 2006, now U.S. Pat. No. 7,955,614, which is a continuation of U.S. application Ser. No. 10/243,787, filed Sep. 13, 2002, now abandoned, which claims the benefit of U.S. Provisional Application No. 60/371,290 filed on Apr. 9, 2002, entitled "Microfabricated Nanopore Device for Sustained Release of Therapeutic Agent" and U.S. Provisional Application No. 60/322,160 filed on Sep. 14, 2001, entitled "Microfabricated Nanopore Device for Sustained Release of Therapeutic Agent," the disclosures of which are fully incorporated by reference in their entirety as if fully rewritten herein.

TECHNICAL FIELD OF THE INVENTION

The present invention relates generally to drug delivery devices designed to be implanted in the body and specifically to an implantable drug delivery device that utilizes a nanopore membrane fabricated to include arrays of channels having precise geometry for controlling the release of a therapeutic agent into the body.

BACKGROUND OF THE INVENTION

The biotechnology industry has created a number of successful biological drugs for treating chronic medical conditions. Such drugs include including alpha epoetin (Procrit®, Epogen®) for treatment of chronic anemia associated with cancer chemotherapy, granulocyte colony stimulating factor (Neupogen®) for treatment of neutropenia associated with cancer chemotherapy; alpha interferon (Intron® A, Roferon® and Infergen®) for treatment of chronic hepatitis; and, beta Interferon (Avonex®) for treatment of relapsing multiple sclerosis.

Although these products provide important benefits to patients and generate sales measured in billions of dollars, these and most other biological drugs have two major limitations: (i) due to their large molecular weight (e.g., >10,000 Daltons) and fragility, such drugs cannot be delivered to the patient by the oral route, and thus, injection is the only method of administration; and (ii) their typically short half-life results in the drugs being quickly cleared from the body, and therefore, they must be administered to the patient frequently (e.g., daily or, three times per week).

In the hospital setting, intravenous administration is usually a safe and reliable method for administering biological drugs. In medical situations where hospitalization or physician visits are not necessary, patients often self-administer biological drugs by subcutaneous or intramuscular injection several times a week over the course of therapy. However, this type of therapy is generally associated with pain at the site of injection, injection site reactions, infections, and lack of compliance with dosing schedule.

Sustained release implants or drug depots provide a potential solution to the medical need for delivering biological drugs for chronic conditions. Sustained release implants have the potential to eliminate compliance as a concern because they provide the physician with the assurance that the drug is being delivered and the patient with the freedom to go about their normal daily activities. Currently, two basic technologies have been developed to address the medical need for sustained release of chronically administered injectable drugs: injectable erodable polymer depots designed to act for several weeks, and implantable devices capable of delivering potent drugs for up to one year. While effective in certain cases, these prior art devices are subject to important limitations.

Sustained release depot formulations that employ polymer depots typically exhibit an initial "burst effect" resulting in the release of up to 90% of the encapsulated drug in the first few days after implantation. Following injection of the device, plasma levels quickly peak and then decline to near constant levels. This characteristic of depots makes them unsuitable for sustained release of a drug over time, where a more constant rate of delivery is desired.

Other prior art implantable devices utilize a semi-permeable membrane to cause osmotic tablets to slowly swell as they absorb water. The swelling tablets push a piston that forces drug from a reservoir out of a small opening. Such devices are capable of sustained release over longer periods of time; however, the number of drugs that are compatible with such devices is limited due to the construction of the device. Thus, only highly potent drugs such as certain hormones can be successfully used with these prior art devices.

Thus, although current technologies provide important advantages over traditional daily injections, a need currently exists for implantable systems that are more flexible with respect to the types, size, stability and solubility properties of drugs themselves, and with respect to the drug delivery patterns achievable using such a device, i.e., avoidance of "burst" effects and achieving a more constant rate of drug delivery.

SUMMARY OF THE INVENTION

These and other limitations of the prior art are overcome by the present invention which provides a drug delivery device that includes a capsule for implantation into the body. This capsule effectively separates the drug or other material that is encapsulated within the device from the environment external to the device. The capsule further includes a reservoir for containing a substance such as a therapeutic agent, at least one port for allowing the substance to diffuse from or otherwise exit the reservoir; and a nanopore membrane in communication with the capsule at or near the exit port for controlling the rate of diffusion of the substance from the exit port. The device also includes a screen for providing structural support to the nanopore membrane and for keeping the pores of the nanopore membrane clear.

The capsule includes a nanopore membrane consisting of an array of parallel channels with precise dimensions typically in the 4 to 100 nm range separating the internal reservoir from the external medium. By precisely tailoring the pores of the membrane to the molecular dimensions of the drug, such nanopore membranes serve to control the diffusion kinetics of the therapeutic agent from the reservoir at a molecular level. Presumably, the rate of diffusion is related to the geometry of the channels which physically constrain the random molecular motion of drug solute molecules in at least one dimension. Thus, the rate of diffusion is slowed and controlled at a nearly constant level as a function of pore size and is less dependent on the concentration gradient. The device is capable of zero-order release of a therapeutic agent after implantation over prolonged periods (weeks to months, or even years). Controlling the dosage delivered to the patient over time is also possible with the present invention.

One embodiment of the drug delivery device includes an osmotic engine for creating a flow of fluid into and through the device. The osmotic engine further includes a semi-permeable membrane incorporated into a portion of the wall of the capsule, and an osmotically active agent admixed with the therapeutic agent. The osmotically active agent is of sufficient molecular weight as to be restricted from passing through both the semi-permeable membrane and the nanopore membrane. The osmotic engine also includes a net flux of water entering the reservoir from the external medium through the semi-permeable membrane and exiting the device through the nanopore membrane.

Drugs therapies that meet the following criteria are good candidates for formulation in the present implant device: (i) those that normally injected intravenously or subcutaneously; (ii) those that require frequent administration over a prolonged period of time (e.g., 2-3 times per week for more than two weeks); (iii) those involving treatment of a serious condition where non-compliance to the prescribed treatment regimen will have serious consequences; (iv) those utilizing sufficiently potent drugs so that the cumulative dose for the period of treatment can fit within a small reservoir; and/or (v) those using a drug with adequate stability to withstand exposure to body temperature for duration of therapy.

Further advantages of the present invention will become apparent to those of ordinary skill in the art upon reading and understanding the following detailed description of the preferred embodiments.

BRIEF DESCRIPTION OF THE DRAWINGS

The accompanying drawings and figures, which are incorporated in and form a part of the specification, schematically illustrate preferred embodiments of the invention and, together with the general description given above and detailed description of the preferred embodiments and examples given below, serve to explain the principles of the invention.

DETAILED DESCRIPTION OF THE INVENTION

I. Drug Delivery Implant Device

The present invention is designed as a small medical implant for sustained, constant release of potent drugs used to treat chronic conditions. An exemplary embodiment is substantially cylindrical in shape and has a diameter of about 4 to 8 millimeters (about 0.125 to 0.25 inches) and a length of about 40 to 80 millimeters (about 1.5 to 3 inches). Preferably, the device is implanted in a manner similar to other medical implants; following administration of a local anesthetic, a physician or other medical professional makes a small (about 5 millimeter) incision in the skin of the upper arm, forearm or abdomen of the patient. Using a sterile implanting tool, the physician inserts the device under the skin of the patient (i.e., subcutaneously) and then covers the incision with a bandage. At the end of the treatment period, the physician removes the implant using a similar procedure.

The drug release device of the present invention is designed to slowly release the encapsulated drug at a nearly constant rate to mimic a slow infusion, so that the patient will have therapeutic levels of the drug in his/her body for the entire course of therapy. The drug reservoir of device contains a highly concentrated form of the drug either as a saturated solution, dry powder or concentrated suspension to minimize the size of the device required to hold the cumulative dose required for an extended period of treatment (e.g., several weeks to 6 months).

Figure 3A:
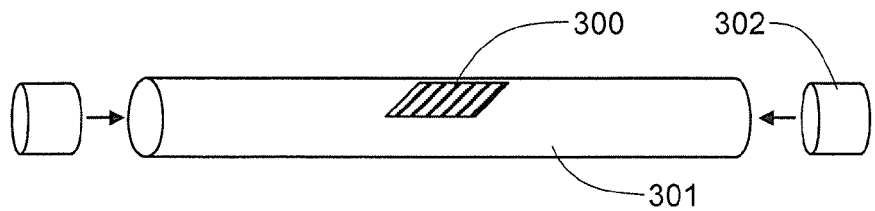
FIG. 3A is a graphic illustration of one embodiment of the drug delivery device of the present invention showing a capsule comprising a segment of thin-walled titanium alloy tubing, sealed at each end with polymer end-caps, and a nanopore membrane fixed to a milled out portion of the capsule.
Figure 3B:
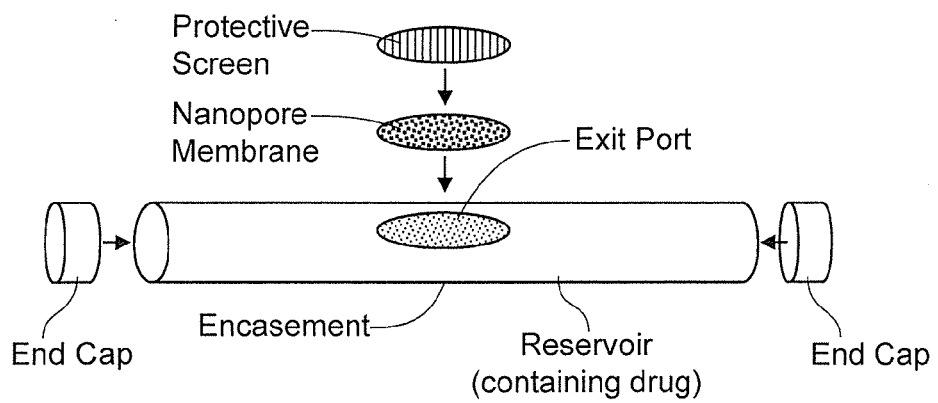
FIG. 3B is a graphic illustration of another embodiment of the drug delivery device of the present invention providing an exploded view of the device and its component parts.
Figure 3C:
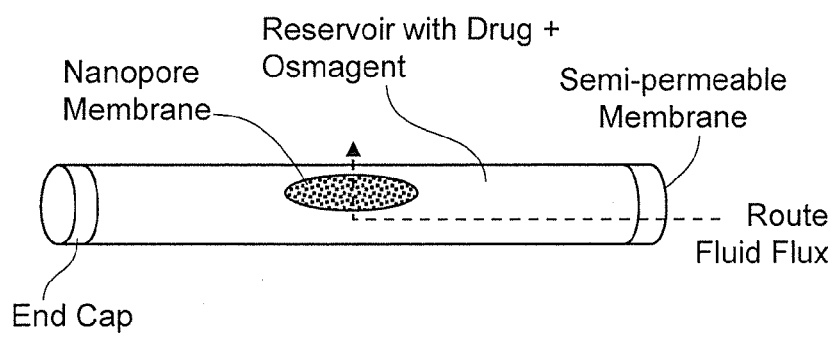
FIG. 3C is a graphic illustration of another embodiment of the drug delivery device of the present invention including a diffusion-facilitating osmotic engine. This embodiment includes a semipermeable membrane and osmagent, which combine to provide passage of water from the external medium, through the reservoir of the device and out the nanopore membrane channel array (indicated by the dotted line).

As shown in FIGS. 3A-3C, an exemplary embodiment of the present invention provides a drug delivery device 10 which includes an encasement or capsule 12 for implantation into the body. Capsule 12 further includes reservoir 22 for containing a substance, such as a therapeutic agent, and at least one port 24 for allowing the substance to diffuse from or otherwise exit the reservoir, and a nanopore membrane 26 attached to, mounted on, or otherwise in communication with capsule 12 and exit port 24 for controlling the rate of diffusion of the substance from exit port 24. In this embodiment, membrane 26 serves as the only diffusion-limiting communication between the reservoir and the external medium.

Optionally, the drug delivery device may include a screen 28 for providing structural stability to the nanopore membrane without affecting the rate of release of a therapeutic agent. This screen is typically made from a porous polymer or other material and may completely or partially surround the capsule, or may be positioned on top of the membrane, on the bottom of the membrane, or both on the top and bottom of the membrane. Screen 28 also prevents fouling/blockage or cellular infiltration of the pores of nanopore membrane 26. In one embodiment the entire capsule is coating with a porous polymeric material to protect the device and provide a biocompatible interface.

An exemplary embodiment of the capsule of the drug delivery device of the present invention is an impermeable, non-deformable, biocompatible capsule which further includes a first open end 14; a second open end 18; a first polymeric end cap 16 for closing first open end 14; and a polymeric second end cap 20 for closing second open end 18. The open ends are useful for filling reservoir 22 with a therapeutic agent or other substance. In one embodiment, the end caps are tapered such that when attached to each open end of the capsule, both ends of the capsule are bullet-shaped. Capsule 12 may be substantially cylindrical in cross-section or substantially elliptical in cross-section. A semi-triangular anti-rotation device may be attached to each end of the capsule, or anywhere along the length of the capsule, for preventing side-to-side rotation of the capsule following implantation of the drug delivery device. Capsule 12 may be manufactured from titanium alloy, surgical grade stainless steel, or a polymeric material.

The drug delivery device of the present invention is designed for implantation in the body subcutaneously, in a defined anatomical compartment of the body, at a pathological site, or at combination of sites. Suitable sites include the peritoneal cavity, brain, plural cavity, surgical site, pathological site, pericardium, inter articular space, eye, and/or subarachnoid space (C SF).

In an exemplary embodiment, capsule 12 is typically made of segments of standard thin-walled stainless steel or titanium alloy tubing in which a flat area has been milled to serve as the seat for nanopore membrane 26. Nanopore membrane 26 is mounted over this area of the device under protective screen 28. In one embodiment, drug delivery device 10 is about 4 to 10 mm in diameter and about 45-100 mm in length with an internal volume of approximately about 250 µL, to several milliliters depending on the thickness of the tubing.

In another embodiment, a small area of the capsule wall includes openings (pores or slits) with dimensions too large to restrict diffusion of even the largest molecules. These openings serve as non-diffusion-limiting exit ports within the capsule wall and protect internal components of device 10. In this embodiment, nanopore membrane 26 is seated next to or near an opening in the wall of a tubular inset, the outer diameter of which is similar to the inner diameter of the capsule. The inset tube segment is inserted into the interior space of the capsule and the nanopore membrane array is positioned beneath the openings. The inset tube is configured with o-rings, which serve to seal the space between the capsule openings and the surface of the nanopore membrane. As with the embodiment detailed above, nanopore membrane 26 again serves as the only constraint to free passage into the reservoir filled with the therapeutic agent from the environment outside of or external to the capsule.

As stated, drug delivery device 10 is designed to contain a volume of therapeutic agent or other substance in reservoir 22. In an exemplary embodiment, the capacity of the drug reservoir is approximately 500 µL. The therapeutic agent may be present in a variety of forms including, but not limited to, an aqueous solution, an aqueous crystalline suspension (slurry), a micronized suspension. These solutions or suspensions may be formed within reservoir 22 immediately before implantation of device 10 by hydration of a dry form of the therapeutic agent, or by hydration after implantation of device 10 by inflow of a biological fluid from the medium surrounding the device.

Suitable therapeutic agents include biologically active macromolecules such as peptides, protein drugs, or a polynucleic acids. Suitable peptides or protein biopharmaceuticals include: hormones, hormone agonists, hormone antagonists, growth factors such as CSF. EPO, and growth hormone, cytokines such as the interleukins, immune modulators such as interferon gamma and interferon beta, anti-infectives such as interferon alpha 2b, anti-inflammatories, immune suppressant/anti-rejection drugs, antibodies, anti-arthritic drugs, and anti-tumor agents. Suitable polynucleic acids include: DNA, RNA, plasmid molecules, antisense DNA, and ribozymes. Small molecular weight molecules are also compatible with the present invention. Suitable small molecular weight molecules include, but are not limited to, pain medications or anti-psychotic agents.

In an exemplary embodiment, drug formulations are filled into device 10 as a liquid solution; however, if necessary more highly concentrated forms including a slurry consisting of an insoluble drug suspension, dry powders or centrifuged pellets may be used. For certain unstable drugs, such as certain proteins and peptides, the drug may be co-formulated with a bulking agent such as lactose and loaded into the reservoir of the device as a liquid. After loading the drug/lactose solution may be freeze-dried in situ, providing a dry storage form for the drug within the device reservoir. Excipients may be added to improve drug loading such as polymers, ion-exchange beads, affinity matricis, cyclodextrins, surfactants and the like. Co-solvents such as ethanol and DMSO may also be employed for the purpose of loading additional drug.

Preferably, stabilizers co-formulated with therapeutic agent contained within reservoir comprise water miscible solvents, or polymers of sufficiently high molecular weight and/or shape as to be retained within capsule reservoir because they cannot pass out through nanopore membrane 26. Suitable stabilizers include, but are not limited to carbohydrates, dextrans, polyvinyl pyrrolidone, gum arabic, polyethylene glycol, albumin, dendritic polymers, cross-linked polymer matrix, and surfactants.

II. Nanopore Membrane

Prior art nanopore membrane designs (referred to as the "Berkeley" design) include arrays of C-shaped annular, or rectangular channels with precise dimensions which in their smallest aspect, are in the 4-100 nm range. C-shaped annular pores which are approximately 9 µm in circumference with 2 anchor regions result in a low porosity (0.26%) for a typical 25 nm pore membrane. The minimum reported pore size produced by the Berkeley design was 18 nm. In the original Berkeley design, the pores were produced in a 1.4 by 3.4 mm area (4.76 mm$^2$) within a 6 by 8 mm, rectangular-shaped solid silicon die region. U.S. Pat. Nos. 5,651,900, 5,770,076 and 5,849,486 disclose microfabrication techniques compatible with the present invention and are hereby incorporated by reference in their entirety.

One aspect of the present invention is based on the unexpected finding that such membranes can be tailored to control the rate of release of drugs from an implantable device. By precisely fabricating pores with dimensions that are selected to range from a size similar to that of the drug molecule to several times the size of the drug, (e.g., approximating 1 to 5 times the Stoke's diameter of a drug molecule), nanopore membranes can be used to control diffusion at a molecular level by providing release kinetics which approach zero-order. Zero-order refers to a rate of diffusion that does not change as the concentration gradient decays. To achieve suitably sized pores, the nanopore membrane includes a microfabricated array of parallel channels, wherein the smallest aspect of the channels is selected to provide a constant rate of release of the drug or other substance.

Figure 1:
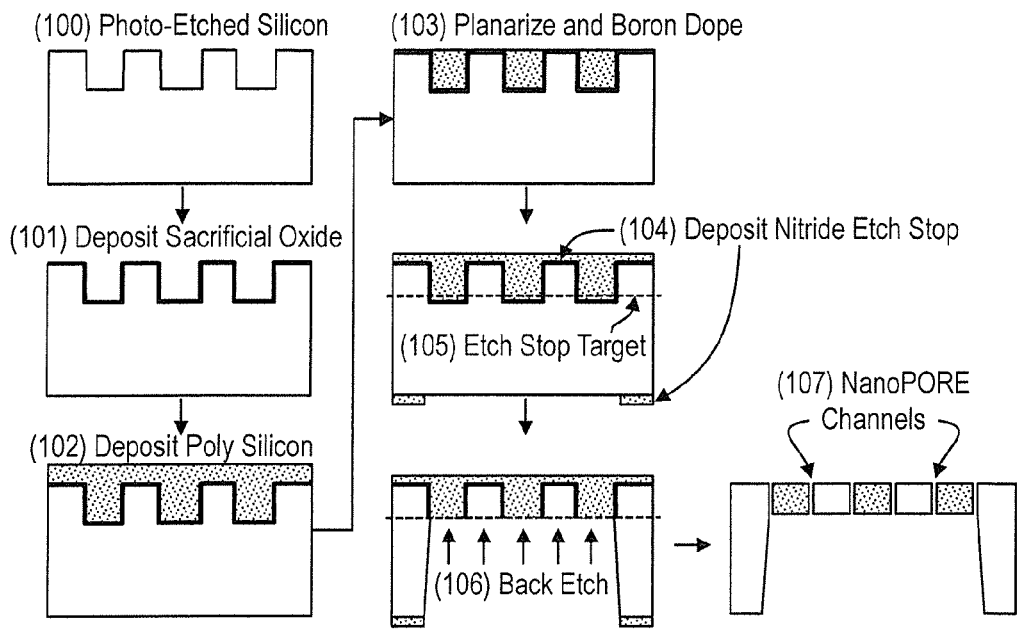
FIG. 1 is a graphic representation of the basic steps in the microfabrication of the nanopore membrane of the present invention.
Figure 2:
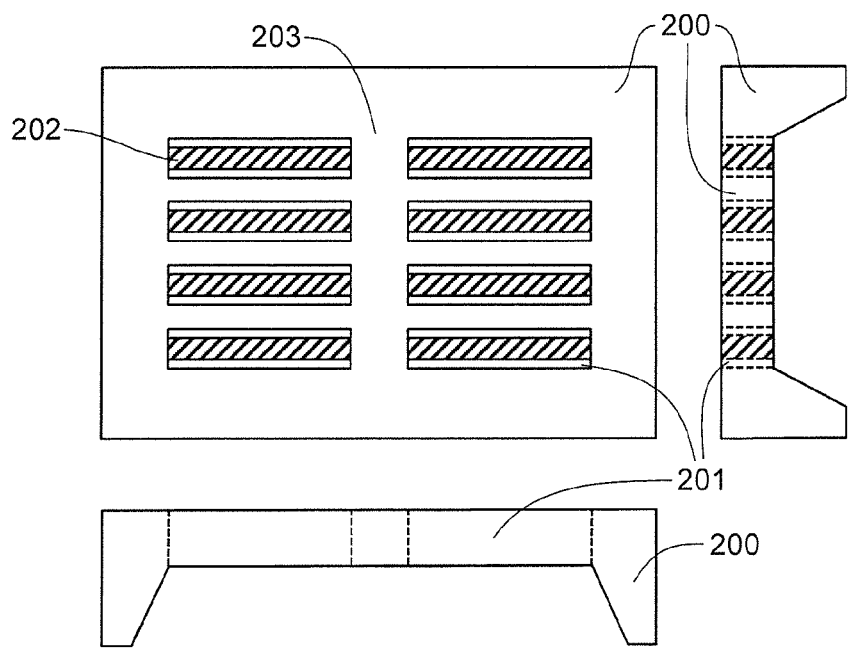
FIG. 2 is a graphic illustration of the basic structural features of the nanopore membrane; both a top view and a side view are presented.

The exemplary embodiment of the present invention was created using the basic microfabrication approach pioneered at Berkeley. However, as shown in FIGS. 1 and 2, the exemplary embodiment includes a novel parallel-pore design. This pore design comprises a series of parallel, rectangular-shaped, 45 µm long channels that are separated lengthwise by 10 µm anchor regions (FIG. 2). The width of these rectangular channels is typically selected at fixed values in the 2 to 100 nm range. Using a 2 pore spacing in the width direction, a high membrane porosity of 1% is achieved for the same 25 nm pore size. Pore sizes down to 4 nm have been produced by this approach. The die layout is also changed relative to the Berkeley design. A similar large-die design is produced with 6 by 8 mm overall dimensions, but the pore area is increased to 2 by 3.5 mm (7 mm$^2$). A smaller membrane die is also produced. In this case, the membrane area is 1 by 2 mm (2 mm$^2$) within a 3 by 4 mm solid die area.

For the purposes of the present invention, microfabrication facilities available at The Case Western Reserve University (CWRU) in Cleveland, Ohio were used to produce several batches of the new nanopore membrane design. This procedure uses a combination of photolithography and deposition/selective removal of sacrificial layers. The pore size itself is determined by the deposition and selective removal of a sacrificial layer (silicon dioxide) sandwiched between two silicon structural members as in FIG. 3. Using this approach, a selected array of parallel membrane pores, with a specific pore size, density, and path length parameter, is fabricated as desired.

The method for fabricating nanometer-sized (nanometer wide and 45 um long) channels consists of three basic steps: (1) surface micromachining of the nanochannels in a thin film on the top of a silicon wafer by depositing a nanometer-thick sacrificial oxide layer between two silicon structures; (2) forming the membrane by etching away the bulk of the silicon wafer underneath the thin-film structure, and (3) etching the sacrificial layer to form nanometer-sized pores in the membrane. Silicon, poly silicon, a combination of silicon materials, polymer, and co-polymer are all useful for fabricating the nanopore membrane using the techniques described.

The first major process step (see FIG. 1) involves photo or plasma-etching continuous channels in the silicon substrate over its entire surface to define the overall pore shape 100. The etched channels are typically 2 µm wide separated by 2 µm and the depth of these channels defines the membrane thickness of 5 After forming the channels, the next major step involves growing a sacrificial thermal oxide layer over the entire wafer surface including the surface area of the channels 101. The oxide layer thickness defines the pore size in the final membrane. Precise control is needed at this step to assure a uniform, known pore size. Thermal oxidation gives pore size (width) control with sub-nanometer resolution across the entire 4-inch silicon wafer. Etching away the thermal oxide in selected areas of the channel forms anchor regions. The distance between these anchor regions defines the pore height (45 µm).

A polysilicon structural layer is then deposited over the channels 102 and planarized to allow access to the nanopore channels from the front face of the array 103. Following a boron-doping step to create a KOH etch stop 105, a silicon nitride protective layer is deposited and windows are opened in this layer on the backside of the wafer 104. The bulk silicon is removed through these etch windows up to the etch stop layer of the array using KOH 106. This bulk etch defines the membrane area and dye shape. The structure is then released by etching the protective nitride layers and the sacrificial oxide layers in a concentrated HF bath 107.

The major structural component of the nanopore membranes created by this approach is illustrated diagrammatically in FIG. 2. An array of parallel rectangular channels is formed 201 between alternating silicon 200 and polysilicon 202 structural layers following the removal of the sacrificial oxide layer. Anchor regions 203 which lie between the channel arrays provide mechanical strength.

Two batches of membranes were fabricated for the present invention. Table 1 provides a list of the number of membrane dies produced. In this table, the batch number is listed along with the number of both large and small dies produced with a given pore size. In all cases, the pore depth is 4.5 µm. Note that both large and small-sized dies were produced and that these membranes have a variety of pore sizes in the 2 to 100 nm range.

TABLE 1

| Nanopore Membrane Dies | | | |
| --- | --- | --- | --- |
| | Nominal Pore | Number of Dies | |
| Batch Number | Size, nm | Small | Large |
| 2 | 4 | 121 | 53 |
| 1 | 7 | 391 | 263 |
| 1 | 13 | 340 | 268 |
| 1 | 20 | 92 | 69 |
| 1 | 27 | 116 | 79 |
| 1 | 47 | 72 | 24 |
| 1 | 49 | 187 | 136 |

Other embodiments of the nanopore membrane of the present invention incorporate the following characteristics, which presumably improve or enhance the durability of the membrane: (i) a multi-directional pore pattern rather than orienting all the pores parallel in only one direction which tends to increase stress; (ii) reduced membrane area; (iii) incorporation of membrane material that is stronger than silicon such as silicon carbide; and (iv) the additional of a hexagonal honeycomb support structure to the surface of the membrane that increases its effective thickness without changing the pore length membrane thickness.

III. Osmotic Engine

Release of a therapeutic agent from the drug delivery device of the present invention is based on a constrained diffusion mechanism. That is, the rate of diffusion of the therapeutic agent through a static aqueous phase filling the channels of the nanopore membrane is restricted by the width of the channels. It is possible to facilitate or "boost" diffusion through such channels by providing a net movement or flux of fluid in an outward direction relative to the drug reservoir, through the nanopore channels. Such a fluid flux may be provided by equipping the device with an osmotic engine. Therefore, in an alternate embodiment of the present invention the diffusional release mechanism of drug delivery device 10 is facilitated by incorporation of an osmotic engine into the device described above.

With reference to FIG. 3C, this osmotic engine includes (i) a semi-permeable membrane 30 incorporated into a portion of the wall of the capsule, wherein the membrane is permeable to the passage of fluid present in the environment external to capsule 12 and substantially impermeable to the passage of the therapeutic agent in reservoir 22; (ii) an osmotically active agent admixed with the therapeutic agent, wherein the osmotically active agent is of sufficient molecular weight as to be restricted from passing through both the semipermeable membrane and the nanopore membrane; and (iii) a net flux of water entering the reservoir 22 from the external environment through semi-permeable membrane 30 and exiting through the nanopore membrane.

The osmotic engine consists of two basic elements. The first is a semi-permeable membrane introduced into a portion of the containment wall of the capsule. For example, one (or both) of the solid end caps depicted in FIG. 1 may be substituted with a plug made of a semi-permeable material such as cellulose acetate (see FIG. 9). Such a membrane permits entry of fluid from the medium or environment surrounding device 10, but prevents the release of solutes contained within the reservoir 22. Listings of suitable semi-permeable membrane materials and permeability-modifying additives are found in U.S. Pat. Nos. 4,077,407 and 4,874,388, and are available from Eastman Chemical Company (Kingsport, Tenn.). Precast cellulose acetate and other cellulose ester membrane sheet stock are available from Polymer Extruded Products (Newark N.J.) and LAM Technologies (Berlin Conn.).

The second component of the osmotic pump is an osmotically active agent, or osmagent, admixed with the therapeutic agent. The osmagent is of sufficient molecular weight as to be restricted from passage through both the semi-permeable membrane and the nanopore membrane and thus is substantially retained within reservoir 22. The osmagent preferred for biologically labile protein therapeutics comprises a water-miscible, liquid polymer in which a dry, micronized form of the drug is suspended. Thus, the osmagent may be linear or branched water miscible polymers of MW 5000 to several million Daltons, including but not limited to, dextrans, maltodextrins, albumin, starches, polysucrose, Ficoll, dendritic polymers, hyaluronic acid, polyvinyl alcohol, polyethylene oxide-polypropylene oxide copolymers, polyethylene glycol, and polyvinylpyrrolidone. The osmagent may also be fluid polymers up to 50:50 mixture by weight including but not limited to: Pluracol V-10, a member of the UCON lubricant series, a member of the Pluronic surfactant series, or a member of the Tetronic surfactant series.

The present invention is intended to release encapsulated drug at physiologic temperatures and over time frames ranging from weeks to months. Some clinically important biologically active protein therapeutics may be unstable in aqueous solution under such conditions. While the therapeutic agent may be formulated as an aqueous or crystalline suspension which may or may not include stabilizers such as those described above, a preferred osmotic engine design for biologically labile protein therapeutics is a dry, micronized form of the drug suspended in the anhydrous, water-miscible, liquid polymer osmagent. A drug used with this embodiment may be micronized by any number of methods known to the art such as spray drying, freeze drying and/or milling. The micronized drug and osmagent are mixed to create a suspension that is filled into the device reservoir. The osmagent may be mixed with a small fraction of water (for example, up to 50:50 by weight) if desired, for example, to change viscosity and/or to prime the system for diffusion-based operation.

The osmagent creates a colloid osmotic pressure within reservoir 22, attracting water from the external medium. Capsule 12 is not expandable and thus the volume of the reservoir is held constant. Water entering the device through semi-permeable membrane 30 under the influence of the osmagent is thus forced to exit through the nanopore channels. The rate of flux of water is controllable by (i) the features of the semi-permeable membrane including the material used, additives, inherent water permeability, surface area, and thickness, and (ii) the nature of the osmotically active polymer including the molecular weight, concentration, and osmotic pressure. Methods to calculate permeation rates through semi-permeable membranes under selected conditions are disclosed in U.S. Pat. No. 4,077,407 which is hereby incorporated by reference in its entirety.

Fluid flux provided by such an osmotic engine is used to boost efflux of drug molecules from the drug delivery device when necessary to achieve a desired release profile (i.e., zero-order) and/or desired durations of release. The fluid flux is also intended to maintain the patency of the nanopore fluid channels by inhibiting fouling or clogging of the nanopore channel walls and end-openings. The fluid flux also provides a means to slowly dissolve therapeutic agents which have been loaded into the device reservoir in an insoluble, partially soluble or dry form.

In a preferred configuration, following implantation, external fluid enters the device through semi-permeable membrane 30, under the influence of the water-attracting properties of the polymer osmagent, and exits through the nanopore membrane while the volume of the reservoir remains constant. Entry of water into device 10 slowly solubilizes the exposed surfaces of the micronized drug particles, and small amounts of drug become entrained as a solute in the fluid flow. The amount of water passing through the device at any given time is limited and thus the protein enters solution gradually over time. Since the dry particles dissolve slowly, the stability of the micronized protein drug is preserved. Release of drug molecules from the device is based on diffusion through the fluid phase and is controlled by water flux through the reservoir, the rate of solvation of the drug into the water phase, and by selection of the proper nanopore membrane dimensions (as detailed below). Combined, these features provide a high degree of control over release kinetics.

The osmotic influx of fluid provided by the osmotic engine feature of the present invention also allows for in vitro or in situ activation of the device. For example, during manufacturing, drug delivery device 10 may loaded with a dry form of a protein drug-osmagent admixture to preserve biological activity of the protein drug during distribution and storage. At the time of use, the device may be placed in a sterile aqueous solution, such as PBS or D5W, for a period of time sufficient for entry of a portion of the external aqueous medium into the device reservoir through the semi-permeable membrane. The fluid entering the reservoir dissolves or partially dissolves the protein drug and osmagent and prime the nanopore channels with fluid, thus providing the aqueous pathways required for the constrained diffusion mechanism to operate. The device would then be rinsed with sterile PBS or D5W and implanted. Similarly, a device loaded with a partially dissolved or dry therapeutic agent-osmagent admixture may be implanted into a body compartment such as under the skin. The external fluid medium would enter the device reservoir through the semi-permeable membrane, hydrating the drug-osmagent admixture and priming the nanopore channels. A slight delay in drug efflux is expected as priming takes place.

In summary, the combination of the physical constraints imposed on the diffusion of drug molecules provided by the nanopore membrane geometry, plus the osmotically driven flux of fluid through the device, provides a novel means of tailoring the release kinetics of selected drugs to achieve optimal therapeutic outcomes.

IV. Examples

Controlling the rate of drug diffusion through nanopore membrane 26 is an important aspect of the present invention. Previous research involving nanopore membranes has not recognized the relationship between nanopore membrane geometry and the phenomenon of constrained molecular diffusion. Furthermore, previous research has not suggested the benefits of combining constrained diffusion with an osmotic engine as detailed above. Thus, diffusion studies have been conducted for the present invention to evaluate the applicability of nanopore membranes to constrained molecular diffusion for a small molecule (glucose), a large molecule (albumin), and lysozyme. These studies, detailed in the examples below, provide a demonstration of the ability of nanopore membranes to constrain rates of diffusion over a broad range of molecular weights.

Example 1

Glucose Diffusion

Nanopore membranes with channel widths ranging from of 7 nm to 27 nm were microfabricated from silicon materials according the methods described above. These membranes were placed either in an implant device fitted with nanopore membranes as described above, or placed in a COSART diffusion cell. These diffusion cells consist of two reservoirs with the nanopore membrane sandwiched between. The membrane is sealed by the use of appropriately sized o-rings. The lower reservoir is equipped with inlet and outlet ports through which buffer (such as phosphate buffered saline, PBS) is slowly pumped (using either an HPLC pump or syringe pump). The lower flow cell also contains a stir bar for mixing. A solution of glucose is added to the upper reservoir and fractions of the fluid exiting the lower reservoir collected using a fraction collector or by physically moving the outlet tubing from one empty test tube to another at preset time intervals. The glucose concentration in the fractions is measured using a either a standard glucose monitor or standardized glucose-oxidase assay.

Figure 4:
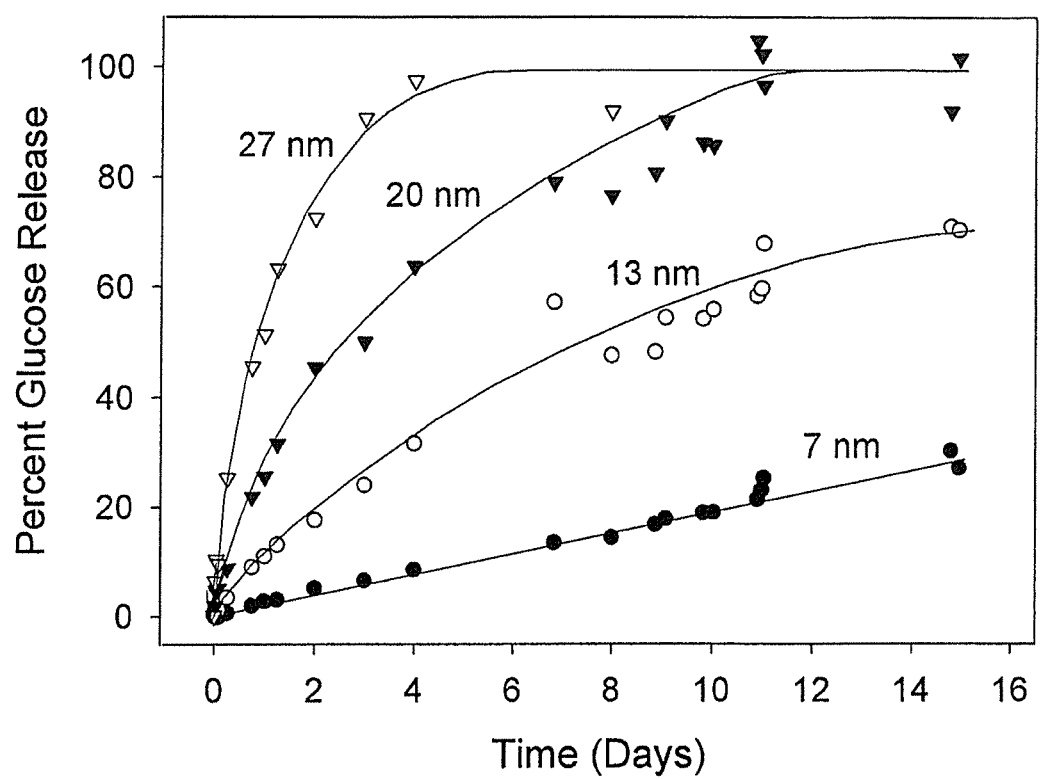
FIG. 4 is a graph showing the relative rates of glucose diffusion through nanopore membranes with pore widths ranging from 7 nm to 27 nm.

The cumulative diffusion of glucose through nanopore membranes of four different channel widths, 7 nm, 13 nm, 20 nm, and 27 nm is plotted in FIG. 4. The shapes of the curves for the 13 nm, 20 nm, and 27 nm membranes indicates that the cumulative movement (flux) of glucose through the membrane is non-linear, and as a consequence the rate slows relative to the initial rate as the concentration gradient across the membranes decays. The rate of glucose diffusion through the 7 nm membrane, however, is linear or zero-order. This pattern is unexpected since the diffusion gradient is decaying with time and thus the driving force for diffusion would be expected to decay as well.

Figure 5:
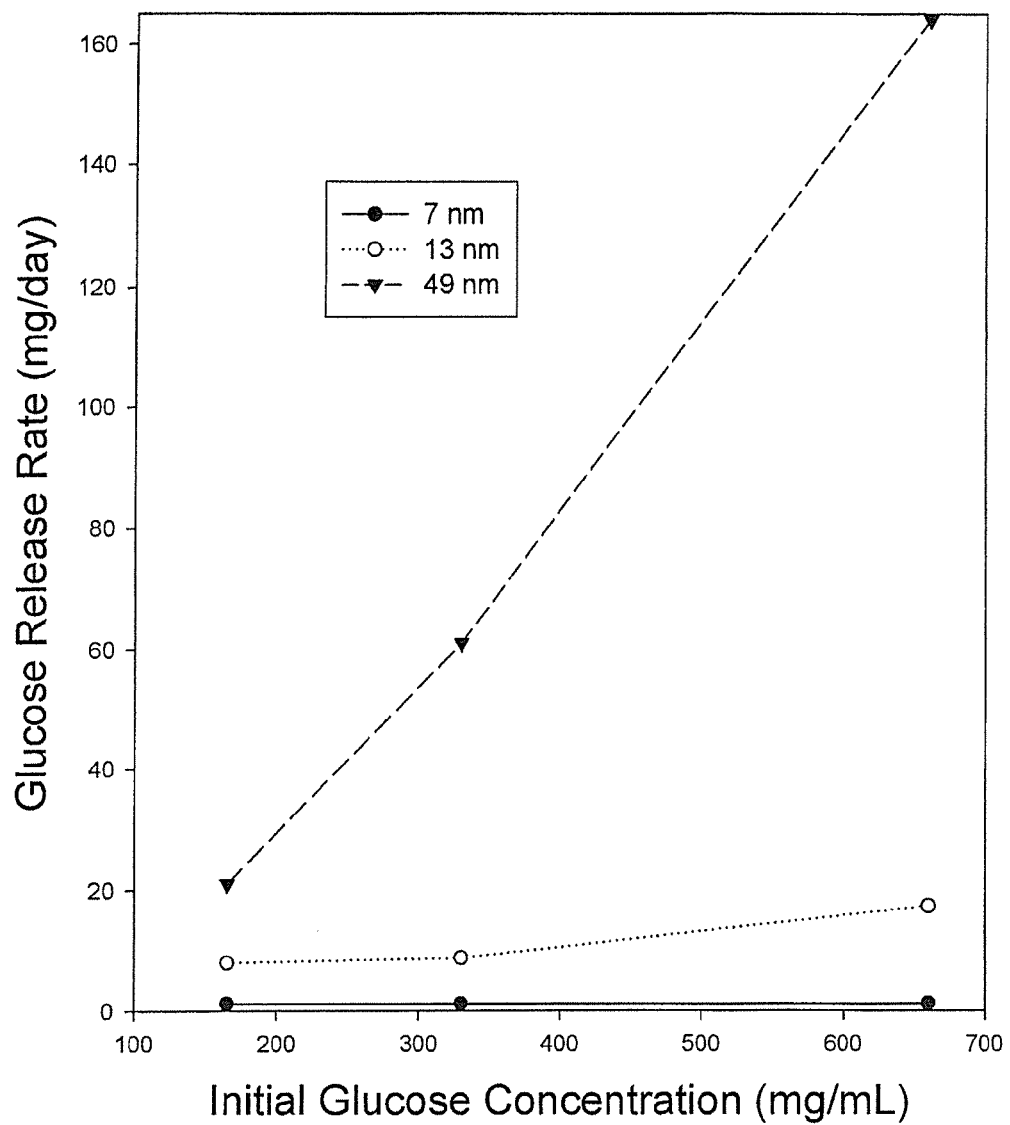
FIG. 5 plots the rates of glucose diffusion through nanopore membranes of sizes 7 nm, 13 nm and 49 nm, as a function of initial glucose concentration.
Figure 6:
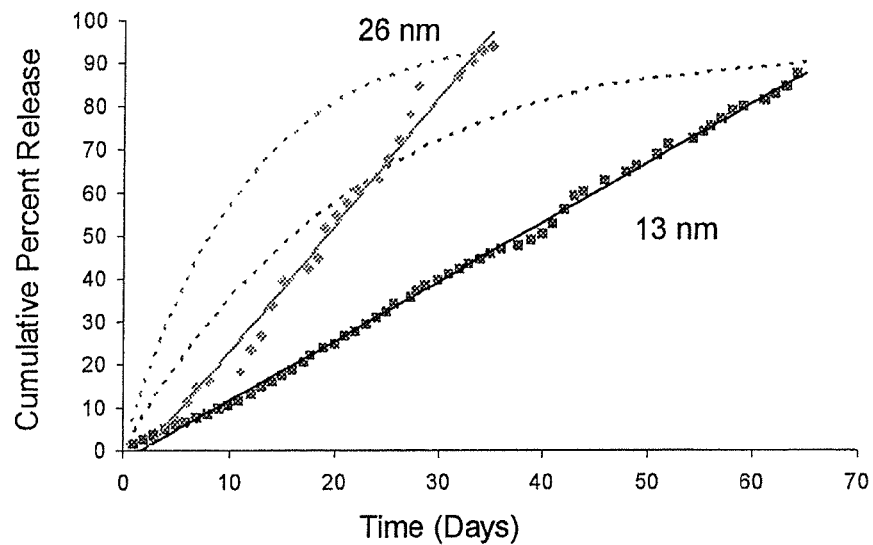
FIG. 6 is a graph showing the cumulative release of $^{125}$-I labeled albumin from two devices similar to the one illustrated in FIG. 3a. The devices are outfitted with nanopore membranes of two pore widths, 26 nm and 13 nm. The dashed lines represent the diffusion rates that are predicted from Fick's laws of diffusion.

The glucose diffusion rate (expressed as mg/day) through nanopore membranes of 7 nm, 13 nm, and 49 nm widths as a function of initial glucose concentration is shown in FIG. 5. For the 13 nm and 49 nm membranes, the rates of glucose flux increases with increasing concentration. In the case of the 7 nm membrane, however, a flux rate of 1.2 mg/day is maintained across a wide range of initial glucose concentrations (i.e., 165-660 mg/mL). These data indicate that glucose diffusion through nanopore membranes with widths of about 7 nm and below is basically zero-order and is not influenced by the magnitude of the concentration gradient across the membrane.

Example 2

Albumin Diffusion

For these experiments, Radiolabeled ($^{125}$I) bovine serum albumin (BSA) was obtained from ICN Biochemicals; Unlabeled BSA was obtained from Sigma Chemical Corp., and microfabricated silicon nanoporous membranes were fabricated as described above.

Implants fitted with nanopore membranes were assembled and loaded with $^{125}$I BSA. Implants were sterilized prior to loading by either autoclaving or chemically sterilizing by soaking in a standard phosphate-buffered saline solution (PBS) containing 0.2% (w/v) sodium azide. The implant formulation was generated by diluting the appropriate amount of $^{125}$I-labeled BSA (determined from the specific activity reported by the manufacturer for each lot obtained) with a 25 mg per mL stock solution of unlabeled BSA. The solution was filter sterilized. The final formulation solution contained BSA at a concentration of 5 mg per mL and a $^{125}$I-labeled BSA concentration of 60-65 µCi per 300 µL, the current approximate loading capacity of each implant.

After aseptically loading the implants with the BSA formulation, each implant was washed by dipping into 25 mL PBS and transferred to a fresh 25 mL PBS, both contained in sterile 50 mL conical tubes. Any residual air bubbles, trapped in the grate opening above the membrane area, were dislodged by moving a stream of liquid containing PBS over the grating with a 1 mL syringe containing a 27 gauge luer-lock needle. A 100 µL aliquot was removed once a day for 3 to 6 days or until the expected constant rate of diffusion was achieved. The aliquot was transferred to a 5 mL polypropylene serum tube and counted on a Packard Gamma Counter.

For each treatment group, three, ten to twelve-week old female Sprague Dawley rats were anesthetized with isoflurane. After shaving and sterilizing the implant site, a 1.5 cm incision was made parallel to and 1 cm from the backbone through the skin layer midway on the animals' flank. A pocket was made for the implant under the skin by opening and closing a pair of hemostats to the front and back of the incision. The incision "pocket" was made in this way to ensure that the ends of the implant did migrate to a position over the incision, limiting the possibility for the ends of the implant to push out through the incision. The implant was rinsed in 2 changes of PBS; the grate of the implant was wetted with 10 uL of PBS. A small amount (100 µL) of PBS was introduced into the pockets for wetting purposes and the implants were inserted into the incision pocket and centered under the incision site. The incision was sutured and the animal was allowed to recover.

A small plastic ring was used to orient the implant membrane downward and in the proper direction relative to the animals' flesh and skin. Release in the proper direction insured that the implant diffusion was not impeded in any way by physical blockage.

For pharmacokinetic analysis, blood sample were obtained. Animals were anesthetized with Isoflurane, the tails warmed for 2 minutes, and 0.2 ml samples of blood were collected from the lateral tail veins. The blood was allowed to clot for 45 minutes, and then spun at 10,000 G for 1 minute, and then a 50 µL, aliquot removed for gamma counting on a Packard Gamma Counter.

Figure 7:
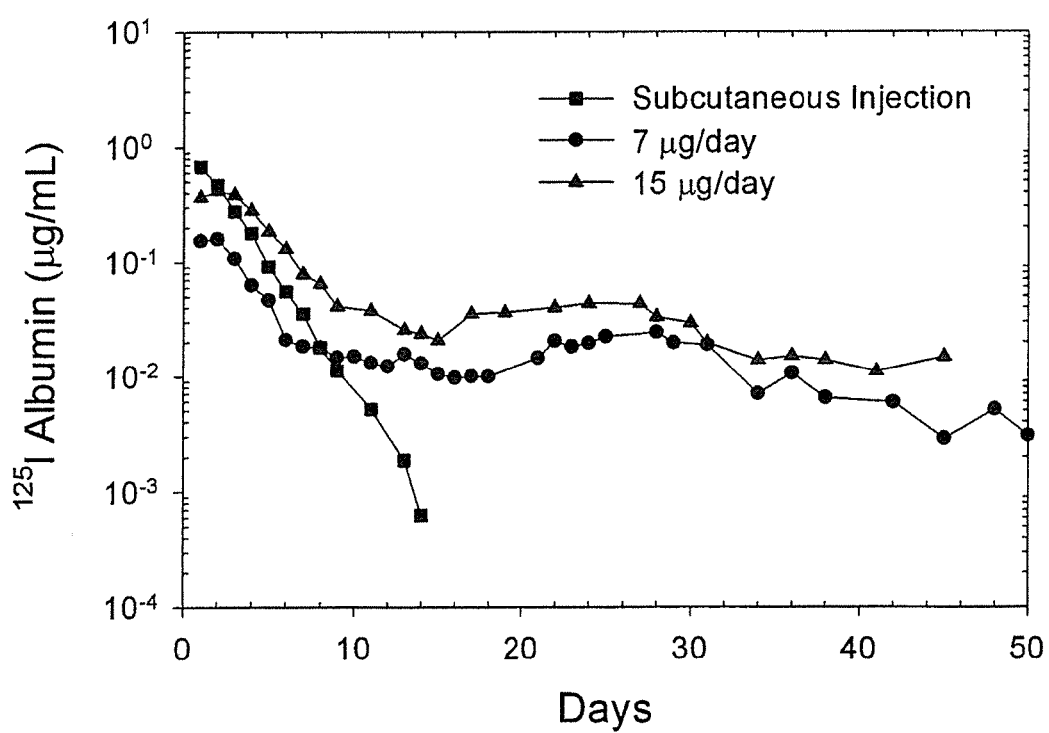
FIG. 7 is a plot showing blood levels of $^{125}$I-albumin in groups of rats given either a subcutaneous injection of 125 micrograms of $^{125}$-I labeled albumin (squares), or implanted with nanopore membrane drug delivery devices designed to release the albumin at rates of 7 μg/day (circles) and 15 μg/day (triangles).

The results of these in vivo experiments, shown in FIG. 7, represent the total calculated amount of BSA measured in the vascular compartment (in µg per mL) of each of the three treatment groups (n=3): subcutaneous injection, or Nano-GATE devices designed to deliver 7 µg/day or 15 µg/day. In the case of the implant groups, a two-phase pattern is seen for BSA clearance from the blood stream. The first phase, represented by data collected between days 2 through 10, shows a rapidly decreasing slope that closely resembles the slope obtained with a 125 [µg subcutaneous (SubQ) injection. This rapid initial clearance of BSA from the bloodstream is very likely due to the extravasation of BSA from capillary beds into the interstitial fluid compartment and eventually the lymphatic system. Equilibration of exogenously administered BSA between the blood and interstitial compartments is a well known phenomenon.

The second phase of BSA serum levels shown in FIG. 7 is represented by data collected between days 10 through 50. During this phase, BSA is slowly cleared from the animals' blood. These data suggest that physiological equilibrium or steady-state is achieved suggesting that the rate of BSA release from the NanoGATE implant is balanced with clearance from the blood stream. This pattern stands in stark contrast to the rapid clearance of the onetime, 125 µg bolus dose of BSA administered via subcutaneous injection.

Example 3

Lysozyme Diffusion

Figure 8:
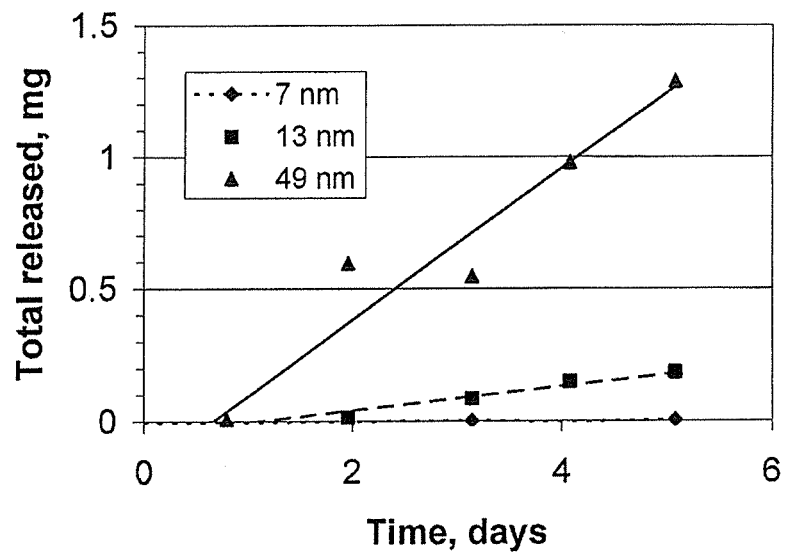
FIG. 8 shows the in vitro diffusion of $^{125}$-I labeled lysozyme as a function of time through nanopore membranes with pore widths of 7 nm (diamonds), 13 nm (squares) and 49 nm (triangles).

Lysozyme, an enzyme with a molecular weight intermediate between that of glucose and albumin (MW 12,000 Daltons) was used to measure diffusion kinetics through nanopore membranes both in vitro and in vivo. Radiolabeled ($^{125}$-I) lysozyme was obtained from ICN Biochemicals. Unlabeled lysozyme was obtained from Sigma Chemical Corp. Radiolabeled lysozyme was admixed with unlabeled lysozyme and loaded into implants as described above for albumin. In vitro release rates for three size membranes are plotted in FIG. 8. Lysozyme release rates are zero-order for membranes pore sizes of 13 nm and 49 nm. Release of lysozyme through the 7 nm membrane implant was virtually undetectable over the time frame tested (5 days). Additional in vitro release testing revealed that, like glucose, at a pore size of 13 nm or less, flux of lysozyme through the nanopore membrane is independent of initial concentration (data not shown).

Figure 9:
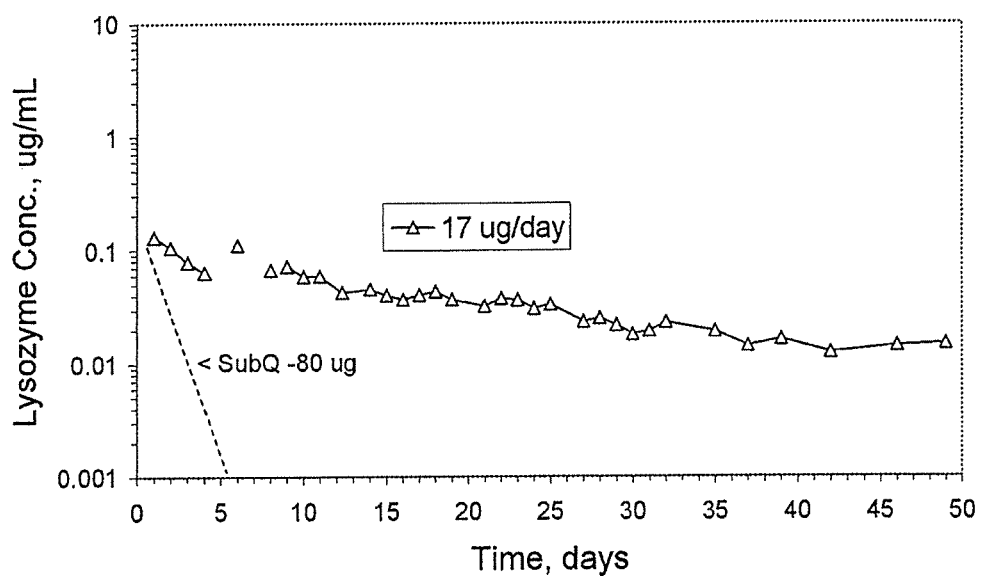
FIG. 9 is graph showing the blood levels over a 50-day period of $^{125}$-I labeled lysozyme in groups of rats after subcutaneous injection of 80 μg of lysozyme (dashed line) or after subcutaneous implantation of a nanopore membrane device designed to release 17 μg/day of lysozyme.

Blood levels of lysozyme in groups of three rats given either a single subcutaneous bolus of 80 µg or after implantation of a nanopore implant device designed to release lysozyme at a rate of 17 µg/day are shown in FIG. 9. Lysozyme given subcutaneously is cleared rapidly from the blood stream of the animals with an apparent half-life of less than several days. In contrast, blood levels in animals in the implant group were maintained for a period of several months.

V. Method of Use

The present invention is useful for delivering a therapeutic agent to the body in a controlled manner, according to the following method. First therapeutic agent is loaded into the device, and then the device is surgically implanted into the patient. As detailed above, an aqueous solution or suspension of the therapeutic agent may be formed in reservoir 22 immediately before implantation by means of hydrating a dry form of the therapeutic agent. An aqueous solution or suspension of the therapeutic agent may also be formed in the reservoir after implantation by introducing a biological fluid derived from the medium surrounding the device into the device.

While the drug delivery device 10 is in use, the rate of release of the therapeutic agent is substantially zero-order and is typically independent of the concentration of the therapeutic agent on the interior of the capsule. The rate of release of the therapeutic agent is substantially constant for a period of several weeks to several months following surgical implantation of the device.

While the above description contains many specificities, these should not be construed as limitations on the scope of the invention, but rather as exemplification of preferred embodiments. Numerous other variations of the present invention are possible, and it is not intended herein to mention all of the possible equivalent forms or ramifications of this invention.

What is claimed:

1. A method for delivering a peptide or a protein, comprising
providing a device comprising a capsule for implantation into the body, said capsule comprising a first end, a second end and a fluid impermeable wall extending from the first end to the second end to define a reservoir; said capsule further comprising an exit port in communication with the reservoir and a nanopore membrane in communication with the exit port, wherein said device comprises a peptide or a protein in the reservoir, said peptide or protein having a Stoke's diameter, and wherein said nanopore membrane has pores between about 1-5 times the Stoke's diameter of the peptide or protein, and wherein an amount of the peptide or protein is contained in the reservoir for release at a rate that approaches zero-order release for a period of several weeks.

2. The method of claim 1, wherein said nanopore membrane comprises an array of parallel, annular channels.

3. The method of claim 2, wherein channels in the array of parallel, annular channels have a pore size of between 2-100 nm.

4. The method of claim 1, wherein said nanopore membrane comprises an array of parallel, rectangular channels.

5. The method of claim 4, wherein channels in the array of parallel, rectangular channels have a width of between 2-100 nm.

6. The method of claim 1, wherein the peptide or protein is dispersed within said reservoir as an aqueous solution or aqueous suspension.

7. The method of claim 1, wherein the peptide or protein is in dry form.

8. The method of claim 1, wherein the peptide or protein is a hormone, a hormone agonist or a hormone antagonist.

9. The method of claim 1, wherein the peptide or protein is a growth hormone or a cytokine.

10. The method of claim 1, wherein the peptide or protein is an immune modulator.

11. The method of claim 1, wherein the peptide or protein is an anti-infective or an anti-inflammatory.

12. The method of claim 1, wherein the device comprises an internal volume of about 250 µL to about several mLs.

13. The method of claim 1, wherein the device is about 45-100 mm in length.

* * * * *